United States Patent [19]
Siochi

[11] Patent Number: 5,663,999
[45] Date of Patent: Sep. 2, 1997

[54] OPTIMIZATION OF AN INTENSITY MODULATED FIELD

[75] Inventor: Ramon Alfredo Carvalho Siochi, Fairfield, Calif.

[73] Assignee: Systems Medical Systems, Inc., Iselin, N.J.

[21] Appl. No.: 670,855

[22] Filed: Jun. 28, 1996

[51] Int. Cl.$^6$ ............................................. A61N 5/10
[52] U.S. Cl. ........................... 378/65; 378/64; 250/492.3
[58] Field of Search .................. 378/65, 64; 364/413.26; 250/492.3

[56] References Cited

U.S. PATENT DOCUMENTS 5,148,032  9/1992  Hernandez ........................... 250/492.1
5,339,347  8/1994  Slatkin et al. ............................ 378/65

OTHER PUBLICATIONS

Faiz M. Khan, Ph.D., "The Physics of Radiation Therapy", 2d ed., pp. 200–206.
Siemens Product Brochure, "Digital Systems for Radiation Oncology", pp. 1–16.
Martin B. Levene, M.D., et al., "Computer–Controlled Radiation Therapy", pp. 769–775, Dec. 1978.
Peter K. Kijewski et al., "Wedge–Shaped Dose Distributions by Computer–Controlled Collimator Motion", pp. 426–429, vol.5, No. 5, Sep./Oct. 1978.
Lee M. Chin et al., "Dose Optimization With Computer–Controlled Gantry Rotation, Collimator Motion and Dose–Rate Variation", pp. 723–729, vol. 9, Dec. 1982.

*Primary Examiner*—Don Wong
*Attorney, Agent, or Firm*—Heather S. Vance, Esq.

[57] ABSTRACT

In a radiation emitting device, particularly in a radiation treatment device (2), the radiation treatment for an object (13) via a radiation beam (1) is determined. The field on the object to be irradiated is inputted and then divided up into sections (220–230). Plates or a collimator are arranged between a radiation source and an object (13) to provide an opening over one of sections (220). A radiation beam (1) is generated and used to treat one of sections (220) with radiation. This is repeated until each of sections (220–230) are treated with radiation.

19 Claims, 6 Drawing Sheets

5,663,999

OPTIMIZATION OF AN INTENSITY MODULATED FIELD

BACKGROUND OF THE INVENTION

1. Field of the Invention

The invention relates to a radiation emitting device, and more particularly to a system and a method for determining an efficient process for radiation treatment.

2. Description of the Related Art

Radiation-emitting devices are generally known and used, for instance, as radiation therapy devices for the treatment of patients. A radiation therapy device usually comprises a gantry which can be swiveled around a horizontal axis of rotation in the course of a therapeutic treatment. A linear accelerator is located in the gantry for generating a high-energy radiation beam for therapy. This high energy radiation beam can be an electron radiation or photon (X-ray) beam. During treatment, this radiation beam is trained on a zone of a patient lying in the isocenter of the gantry rotation.

To control the radiation emitted toward an object, a beam-shielding device such as a plate arrangement and/or collimator is usually provided in the trajectory of the radiation beam between the radiation source and the object. An example of a plate arrangement is a set of four plates which can be used to define an opening for the radiation beam. The beam-shielding device defines a field on the object to which a prescribed amount of radiation is to be delivered. A collimator is a beam-shielding device which could include multiple leaves (e.g., 50 leaves). These leaves are positioned to accurately direct the radiation beam toward the area to be treated with radiation. While these leaves provide accurate direction, they also allow for a small amount of undesirable radiation leakage. This leakage occurs between the leaves.

The delivery of radiation by a radiation therapy device is prescribed and approved by an oncologist. Actual operation of the radiation equipment, however, is normally done by a therapist. When the therapist administers the actual delivery of the radiation treatment as prescribed by the oncologist, the radiation-emitting device is programmed to deliver that specific treatment. When programming the treatment, the therapist has to take into consideration the actual radiation output and has to adjust the dose delivery based on the plate arrangement opening to achieve the prescribed radiation treatment at the target depth in the object. This adjustment can be made according to known calculations, but the therapist normally has to do them manually, which can lead to errors. In the context of radiation therapy, a miscalculation can lead to either a dose that is too low and is ineffective, or that is too high and dangerous; a large error (e.g., a misplaced decimal point) can be lethal.

What is needed is a method, and a corresponding system, for efficient and accurate delivery of radiation treatment. Also, a system which minimizes radiation treatment time and reduces radiation leakage is desired.

SUMMARY OF THE INVENTION

According to the invention, radiation output delivered to an object from a radiation source is controlled. The invention begins by defining a field on the object for irradiation. The field is divided into multiple sections. Each of the sections has defined parameters. Each of the sections is individually treated with radiation by (1) defining an opening between the radiation source and the object and by (2) generating a radiation beam. The opening is placed over one of the sections. This opening is capable of delimiting the radiation beam to the defined parameters of that section. The radiation beam has a substantially lossless beam path from the radiation source to the object. This radiation beam is used to irradiate one of the sections. This treatment is done for each of the sections until the field is irradiated.

DETAILED DESCRIPTION

The invention is described below with primary reference to a system for delivering X-ray radiation to a field on a patient, and for delimiting the field using at least one movable plate or jaw in the beam path from a radiation source. The invention may be used to control the delivery of any type of energy, for example, electrons (instead of X-rays), to any type of object (not just a human patient), provided the amount of energy delivered to the field can be sensed or estimated.

Figure 1:
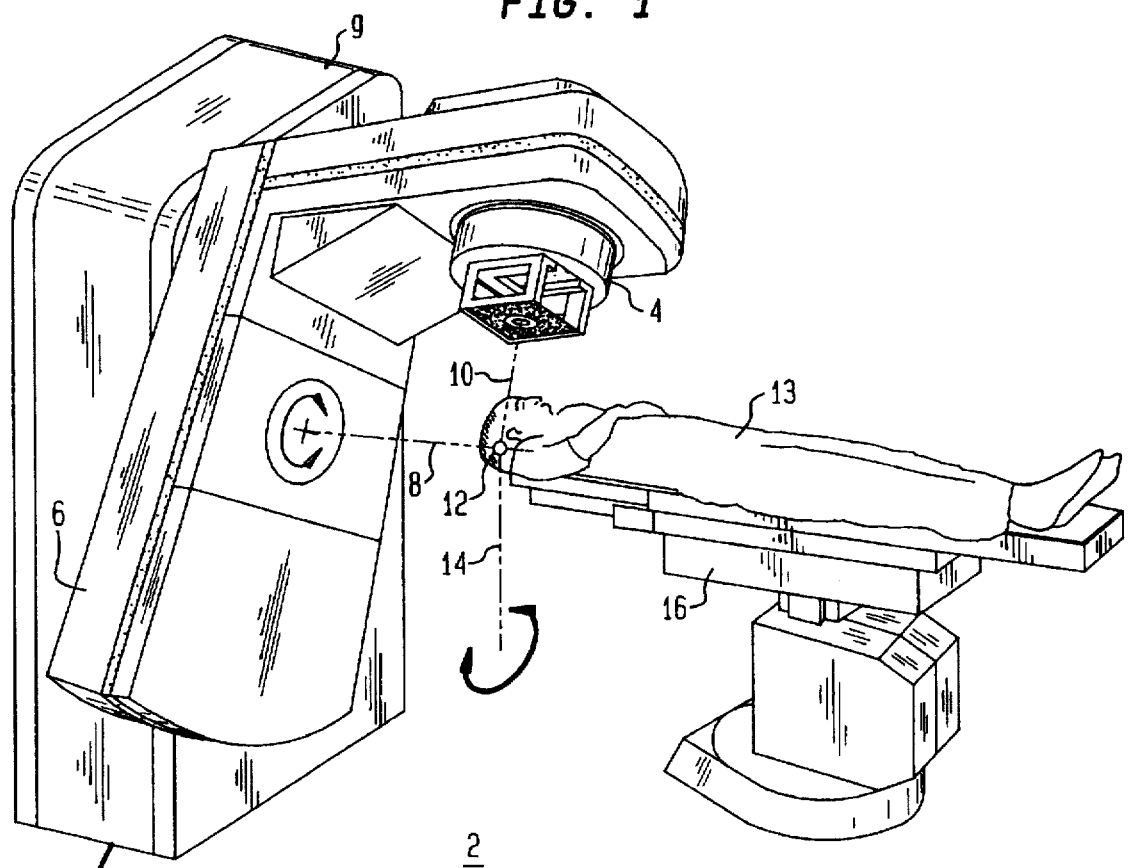
FIG. 1 shows a schematic diagram of a radiation treatment device including a treatment console constructed in accordance with the present invention.
Figure 1:
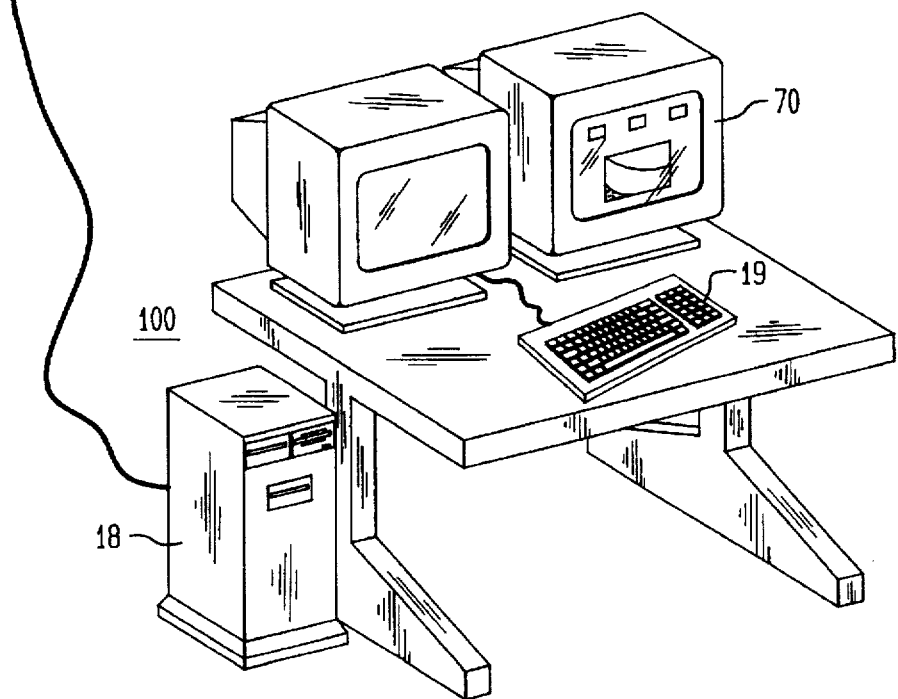

FIG. 1 shows a radiation treatment device 2 of common design, in which plates 4, a control unit in a housing 9 and a treatment unit 100 are used. The radiation treatment device 2 comprises a gantry 6 which can be swiveled around a horizontal axis of rotation 8 in the course of a therapeutic treatment. Plates 4 are fastened to a projection (e.g., an accessory holder) of gantry 6. To generate the high-powered radiation required for the therapy, a linear accelerator is located in gantry 6. The axis of the radiation beam emitted from the linear accelerator and gantry 6 is designated by 10. Electron, photon, or any other detectable radiation can be used for the therapy. During the treatment, the radiation beam is trained on a zone 12 of an object 13 (e.g., a patient who is to be treated, and who lies at the isocenter of the gantry rotation). Rotational axis 8 of gantry 6, rotational axis 14 of the area on the object to be treated, and beam axis 10 all preferably intersect in the isocenter.

The area of the patient that is irradiated is known as the field. The amount of radiation used to treat a field is specified in monitor units (mu). Plates 4 are substantially impervious to the emitted radiation. They are mounted between the radiation source and the patient to delimit the radiation beam to, approximately, the shape of the field. Areas of the body (e.g., healthy tissue) are therefore subjected to as little radiation as possible, and preferably to none at all. In the preferred embodiment of the invention, the gantry can be rotated so as to allow different beam angles and radiation distributions without having to move the patient around. This feature is necessary according to the invention. The invention may also be used with constant radiation delivery rates, and with fixed-angle beams (no rotatable gantry).

Radiation treatment device 2 also includes a central treatment processing or control unit 100, which is usually located apart from radiation treatment device 2. The radiation treatment device 2 is normally located in a different room to protect the therapist from radiation. Treatment unit 100 includes output devices, such as at least one visual display unit or monitor 70, and an input device, such as a keyboard 19. Data can also be input through data carriers, such as data storage devices, or a verification and recording or automatic set-up system 102, which is described below. The treatment processing unit 100 is typically operated by the therapist who administers actual delivery of a radiation treatment as prescribed by an oncologist. By utilizing the keyboard 19, or other input device, the therapist enters into a control unit 76 of treatment unit 100 the data that defines the radiation to be delivered to the patient (e.g., according to the prescription of the oncologist). The program can also be input via another input device like a data storage device, through data transmission, or using the automatic set-up system 102. Various data can be displayed before, during and after the treatment on the screen of monitor 70.

Figure 2:
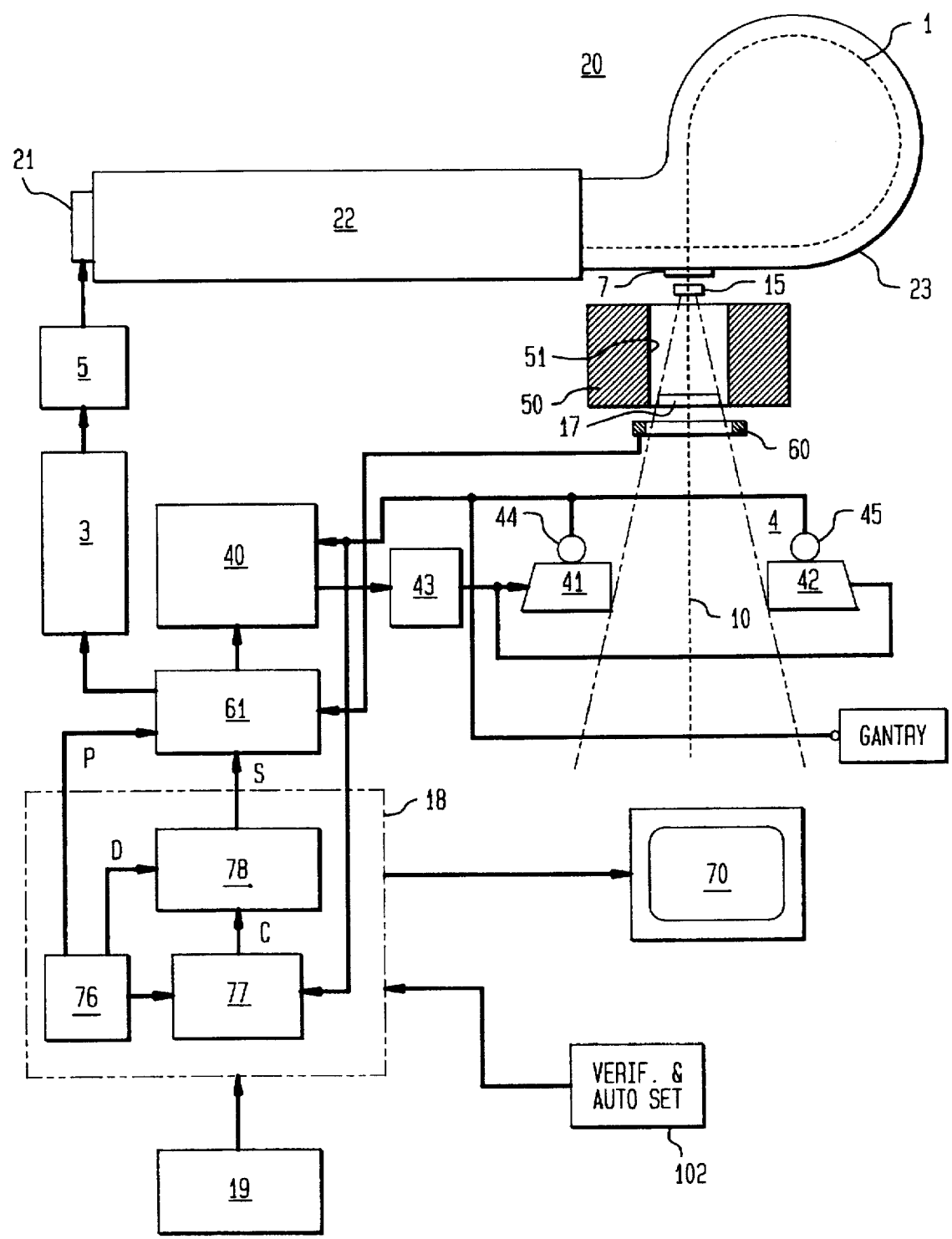
FIG. 2 is a block diagram illustrating portions of a radiation treatment device and portions of a treatment unit in more detail.

FIG. 2 shows portions of a radiation treatment device 2 and portions of treatment unit 100 in more detail. A radiation beam 1 is generated in an accelerator 20. Accelerator 20 comprises a gun 21, a wave guide 22 and an evacuated envelope or guide magnet 23. A trigger system 3 generates injector trigger signals and supplies them to injector 5. Based on these injector trigger signals, injector 5 generates injector pulses which are fed to gun 21 in accelerator 20 for generating x-ray beam 1. The electrons used to produce X-ray beam 1 are accelerated and guided by wave guide 22. For this purpose, a high frequency source is provided which supplies radio frequency signals for the generation of an electromagnetic field supplied to wave guide 22. The electrons injected by injector 5 and emitted by gun 21 are accelerated by this electromagnetic field in wave guide 22 and exit at the end opposite to gun 21 as the electrons which will produce x-ray beam 1. These electrons then enter a guide magnet 23 and from there is guided through a window 7 along axis 10. After passing through a target 15, the electrons produce x-ray beam 1, and this beam 1 goes through a passageway 51 of a shield block 50 and encounters a flattening filter 17. Next, it is sent through a measuring chamber 60, in which the radiation dose is ascertained. Finally, aperture plate arrangement 4 is provided in the path of radiation beam 1. Aperture plate arrangement 4 includes a pair of jaws 41 and 42. As described above, this is just one example of a beam-shielding arrangement that can be used in the invention. The invention will work with others also as long as there is an aperture plate arrangement that defines an irradiated field's shape.

Plate arrangement 4 comprises a pair of aperture jaws 41 and 42 and an additional pair of aperture jaws (not shown) arranged perpendicular to jaws 41 and 42. To match the size of the field to be irradiated, each of the aperture jaws can be moved with respect to axis 10 by a drive unit 43 which is indicated in FIG. 2. Drive unit 43 comprises an electric motor which is coupled to jaws 41 and 42 and which is controlled by a motor controller 40. Position sensors 44 and 45 are also coupled to jaws 41 and 42, respectively, for sensing their positions. This is just one example of such a system. The invention will work with other systems also, as long as there is a beam-shielding arrangement that defines an irradiated field's shape and as long as sensors are provided to indicate the field size. For example, the plates can be replaced with a multi-leaf collimator containing many (e.g., 60) radiation blocking leaves. In the preferred embodiment, a collimator is used for the beam-shielding arrangement.

Motor controller 40 is coupled to a dose control unit 61 which includes a dosimetry controller and which is coupled to a central processing unit 18 for providing set values for the radiation beam for achieving given isodose curves. The output of the radiation beam is measured by a measuring chamber 60. In response to the deviation between the set values and the actual values, dose control unit 61 supplies signals to trigger system 3, which changes the pulse repetition frequency so that the deviation between the set values and the actual values of the radiation beam output is minimized.

Figure 3:
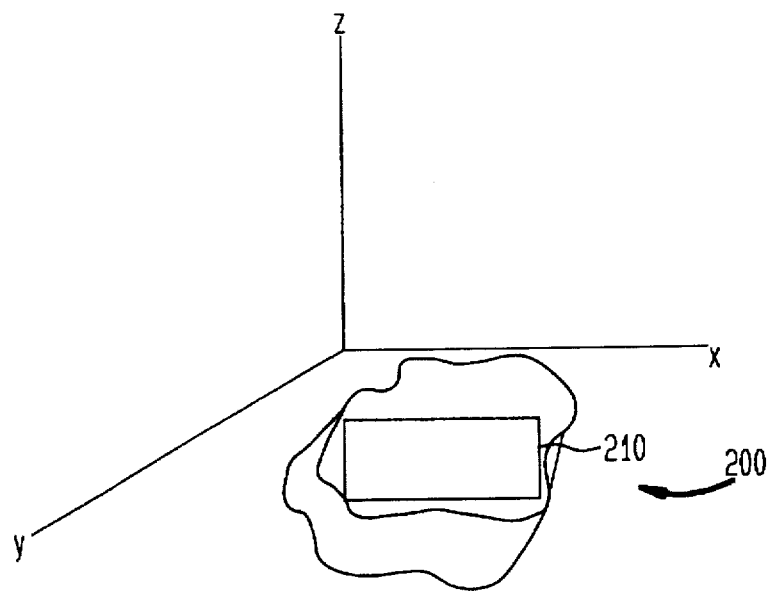
FIG. 3 is a three-dimensional illustration of a field to be treated with radiation.

In such a radiation treatment device, the goal of treating as much of the field as possible without irradiating healthy tissue is prevalent. FIG. 3 is a three-dimensional illustration of a field to be treated with radiation. Three-dimensional intensity map 200 represents one possible field on a patient. The present invention divides intensity map 200 into multiple sections of intensity. Each of these sections is then individually treated with radiation. To effectively treat intensity map 200, more, smaller sections are located near the contoured areas of intensity map 200. For example, one big section (or rectangle in this case) 210 can be used as a base section to cover a large middle section. The areas surrounding big section 210 are then divided up into smaller sections of various sizes. A software program can be used to divide the field into a set of sections which can be efficiently treated with radiation. For example, the movement of the plates can be taken into consideration when the intensity map is divided into sections. The sections can be exposed to radiation more efficiently if plate rotation (or available plate movement) is taken into consideration. The three-dimensional aspects of the intensity map can also be taken into consideration. Thus, the software program optimizes the size and placement of each of the sections along with the order in which the sections will be treated with radiation.

In one embodiment, the intensity map shown in FIG. 3 can be divided by slicing the map into an equal number of monitor units. These static sections can then be reshaped and combined such that the sum of monitor units does not change, and an efficient treatment results. In this situation, a matrix can be used to assist in dividing the field into sections. Instead of dividing and optimizing, the simple intensity map in FIG. 3 can also be effectively treated as one complete area with a multi-leaf collimator. This dividing and optimizing allows for treatment of intensity map 200 with either (1) plates or (2) a combination of plates and a multi-leaf collimator.

Figure 4:
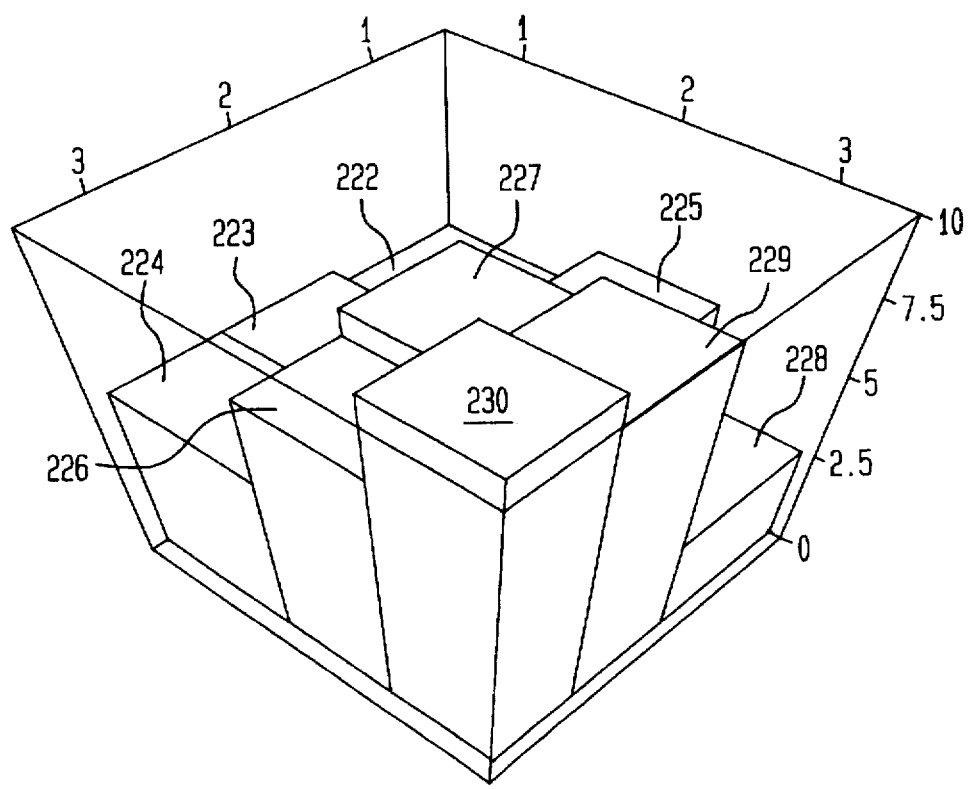
FIG. 4 is another three-dimensional illustration of a field to be treated with radiation.

FIG. 4 is another three-dimensional illustration of a field to be treated with radiation. The numbers in Table 1 are the intensities at locations in space (within a field to be treated) identified by the x and y coordinate system. Rectangular blocks 220–230 are used to represent the different intensities at these locations in space. By placing these distinct rectangular sections 220–230 in a diagram, we get the bar chart like structure in FIG. 4. The height of each of rectangular sections 220–230 is equal to the corresponding section's intensity. Similarly, the position of rectangular sections 220–230 represents the corresponding location within the field.

Table 1 is a matrix identifying the sections in a field to be treated with radiation. All the numbers in the below tables are in monitor units (mu). The four (4) in the upper left-hand corner of the matrix (see Table 1) represents section 222 in FIG. 4. Similarly, the ten (10) in the lower right-hand corner of the matrix represents section 230 in FIG. 4. Therefore, each number in the matrix of Table 1 represents one of sections 220–230.

TABLE 1

| 4 | 6 | 3 |
|---|---|---|
| 5 | 8 | 9 |
| 5 | 7 | 10 |

Table 1 is used by the software program to prepare for treatment. In this example, the matrix in Table 1 is initially broken up into two separate matrices. The first matrix is the section shown in Table 2. This is the largest possible section which can be obtained from the matrix in Table 1.

TABLE 2

| 3 | 3 | 3 |
|---|---|---|
| 3 | 3 | 3 |
| 3 | 3 | 3 |

The second matrix is shown in Table 3.

TABLE 3

| 1 | 3 | 0 |
|---|---|---|
| 2 | 5 | 6 |
| 2 | 4 | 7 |

When the matrices in Tables 2 and 3 are added, the matrix in Table 1 results. The matrix in Table 3 is then broken down into the seven matrices shown in Tables 4–10. These matrices contain only 1's and 0's.

TABLE 4

| 1 | 1 | 0 |
|---|---|---|
| 1 | 1 | 1 |
| 1 | 1 | 1 |

TABLE 5

| 0 | 1 | 0 |
|---|---|---|
| 1 | 1 | 1 |
| 1 | 1 | 1 |

TABLE 6

| 0 | 1 | 0 |
|---|---|---|
| 0 | 1 | 1 |
| 0 | 1 | 1 |

TABLE 7

| 0 | 0 | 0 |
|---|---|---|
| 0 | 1 | 1 |
| 0 | 1 | 1 |

TABLE 8

| 0 | 0 | 0 |
|---|---|---|
| 0 | 1 | 1 |
| 0 | 0 | 1 |

TABLE 9

| 0 | 0 | 0 |
|---|---|---|
| 0 | 0 | 1 |
| 0 | 0 | 1 |

TABLE 10

| 0 | 0 | 0 |
|---|---|---|
| 0 | 0 | 0 |
| 0 | 0 | 1 |

After the matrices have been broken down as shown above, the software program moves some of the 1's around such that some of the matrices can be combined. For example, if the 1 in the upper row of the matrix in Table 6 is moved to another matrix, then the matrices in Tables 6 and 7 can be combined into the matrix shown in Table 11.

TABLE 11

| 0 | 0 | 0 |
|---|---|---|
| 0 | 2 | 2 |
| 0 | 2 | 2 |

Therefore, 1's can be moved around and matrices can be combined to provide for more efficient treatment. In the preferred embodiment, the software program generates a set of static sections with a minimum number of matrices. The matrices are then organized into a specific order. This specific order takes into consideration the movement of the plates (or leaves).

Figure 5:
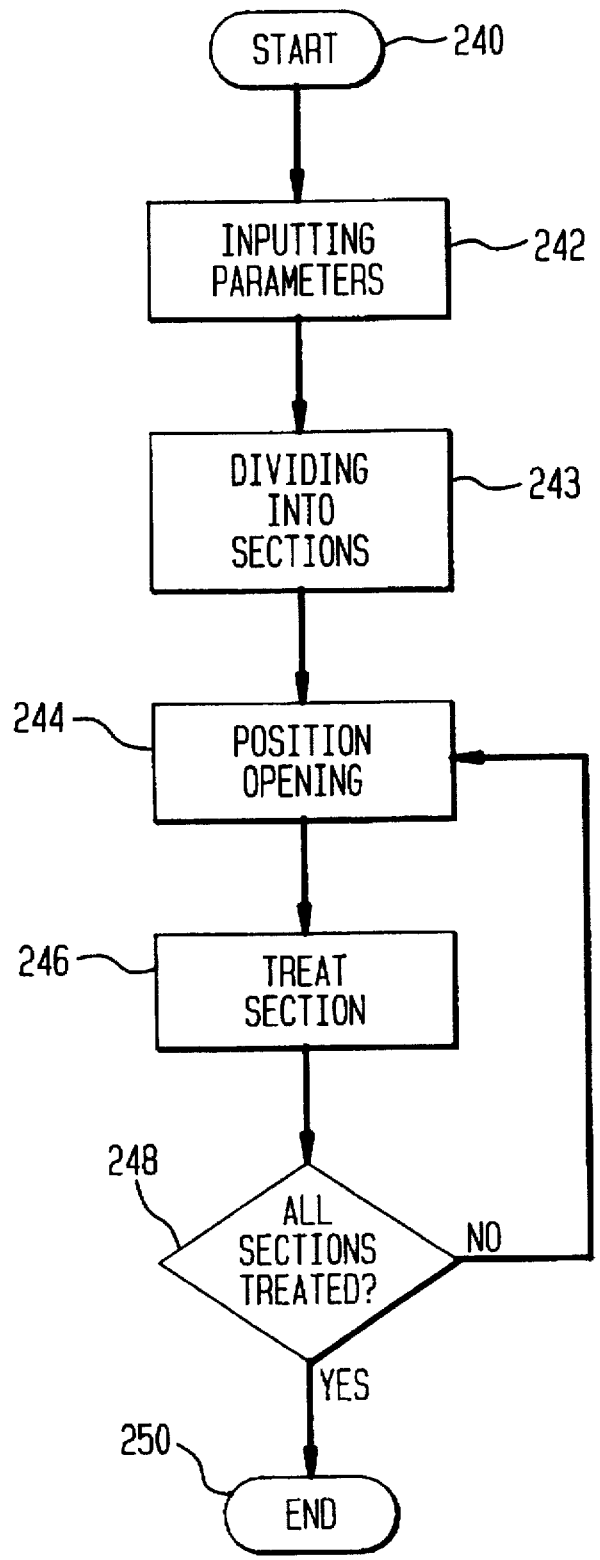
FIG. 5 illustrates a process flowchart for the present invention.

FIG. 5 illustrates a process flowchart for the present invention. At step 240 the software program begins. The parameters of the field to be irradiated are input at step 242. The field is then divided into intensity sections at step 243. As stated above, complex calculations are performed to efficiently divide the field into sections. Now the field is prepared for radiation treatment. The plates are positioned over the first section at step 244, and the first section is treated with radiation at step 246. The software program then checks if all the sections have been treated at step 248. If all the sections have not been treated, the program returns to step 244. The plates are positioned over the next section, and that section is treated with radiation at step 246. This is repeated until all the sections have been irradiated. The software program ends at step 250.

Figure 6:
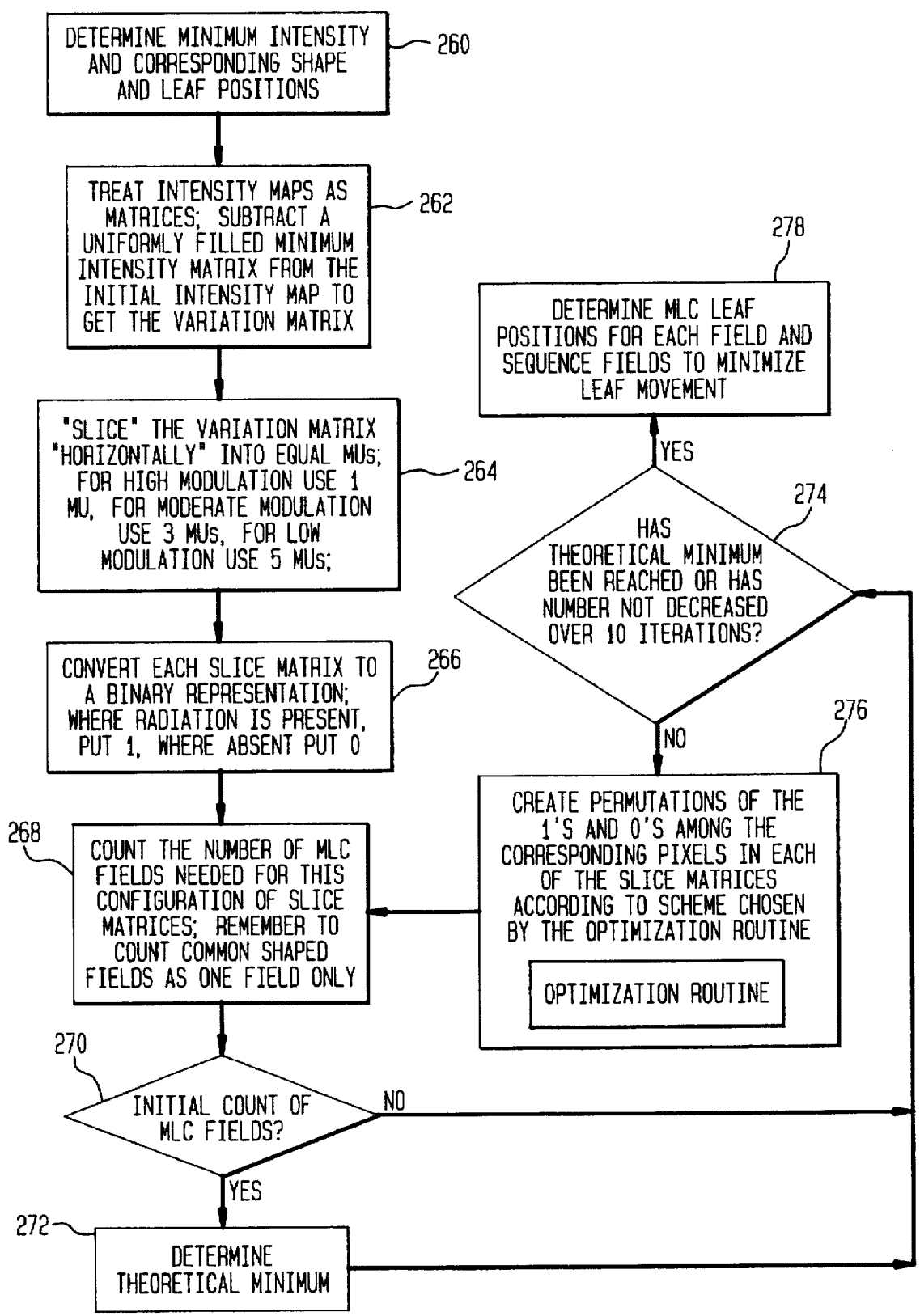
FIG. 6 illustrates a process flowchart for section optimization.

FIG. 6 illustrates a process flowchart for section optimization. FIG. 6 provides more details related to the optimization operation. At step 260, the software program determines the minimum radiation beam intensity, the shape of the field to be irradiated, and the leaf positions in the multi-leaf collimator. The minimum radiation beam intensity will define one section to be irradiated (e.g., see the matrix in Table 2). The leaf positions for the minimum intensity are needed for defining the section shape. At step 262, the intensity map is treated as matrices. A uniformly filled minimum intensity matrix (e.g., see matrix in Table 2) is subtracted from the initial intensity map. This provides a variation matrix (e.g., see matrix in Table 3). At step 264, the variation matrix is sliced horizontally into matrices with equal monitor units (e.g., see matrices in Tables 4–10). The variation matrix does not have a uniform number of monitor units throughout. This variation within the matrix is known as modulation. When an intensity map has low modulation, the shape of the field changes very little as the intensity increases. For example, (1) when high modulation is present, 1 monitor units could be used, (2) when moderate modulation is present, 3 monitor units could be used, and (3) when low modulation is present, 5 monitor units could be used.

At step 266, each of the matrices resulting from the slicing is converted into a binary representation. This binary representation includes a 1 for radiation present and a 0 for radiation absent. At step 268, the number of different plate or leaf positions needed to treat the initial binary matrices is calculated. For this calculation, multiple common shaped fields are treated as only one field. At step 270, the software program checks to see if the theoretical minimum for the initial count of plate/leaf positions has been determined. If not, the theoretical minimum is determined at step 272. If it has been determined, the software program moves to step 274. At step 274, a comparison is made between the number calculated in step 268 and the number determined in step 272. If the number of different plate/leaf positions are greater than the theoretical minimum and the number of different plate/leaf positions has decreased during the last 10 iterations, then the program moves to step 276. If the number of different plate/leaf positions are equal to the theoretical minimum, then the program moves to step 278. In addition, if the number of different plate/leaf positions has not decreased during the last 10 iterations, then the program moves to step 278.

At step 276, permutations of the 1's and 0's in the matrices are created. These permutations are done according to a scheme chosen by the software program's optimization routine. One example of an optimization routine is simulated annealing. Simulated annealing is a known optimization routine that is described in "Numerical Recipes in C," by Press, Teukolsky, Vetterling and Flannery, 1992, Cambridge University Press, pages 444–451. Simulated annealing might take a longer period of time (when compared to other optimization routines), but the results are the most optimal configuration of matrices.

In addition to simulated annealing, an approach which characterizes the intensity map slices in terms of plate/ collimator rotations, "islands," same shape slices, and/or intensity minima could be used. Plate/collimator rotations take into consideration the rotational positions of the gantry. An "island" is an isolated shape in a binary matrix (i.e., a set of 1's without any 0's mixed in between along a direction of leaf motion). For example, in FIG. 7A, matrix 288 is broken into matrices 294 and 296, so that only one "island" is contained in each of matrices 294 and 296. Same shape slices are created when 1s and 0s are redistributed such that matrices become identical and can be combined (as shown in Table 11). Intensity minima are the smallest number of monitor units in a variation matrix. For example, in FIG. 7A, the 1's in the upper left and lower right corners of matrix 284 are intensity minima. In this approach, after the intensity map slices (or initial matrices) are characterized, the intensity minima are moved around (e.g., to matrix 296 in FIG. 7A) until common shaped islands are found. Then, the next higher set of intensity are moved around, and the process repeats until the maximum number of common shaped islands are found. While this approach produces another configuration of matrices quickly, those resulting matrices might not be the optimal configuration of matrices.

After step 276, the software program returns to step 268 which counts the number of plate positions needed for the current configuration of matrices. The software program then goes on to step 270, etc. At step 278, the plate/leaf positions for each section and the sequence for multi-section treatment are determined. This determination is made to minimize plate/leaf movement.

Figure 7A:
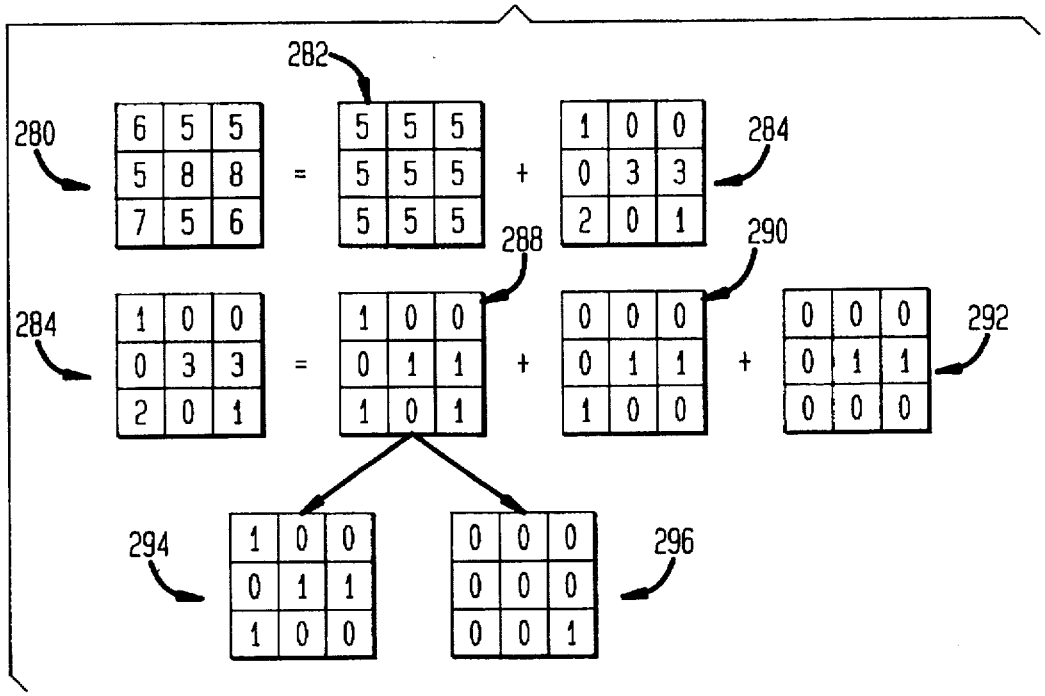
FIGS. 7A–C show matrices used for the section optimization process.
Figure 7B:
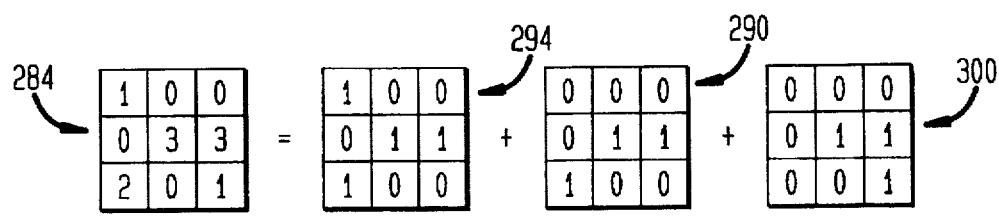
Figure 7C:
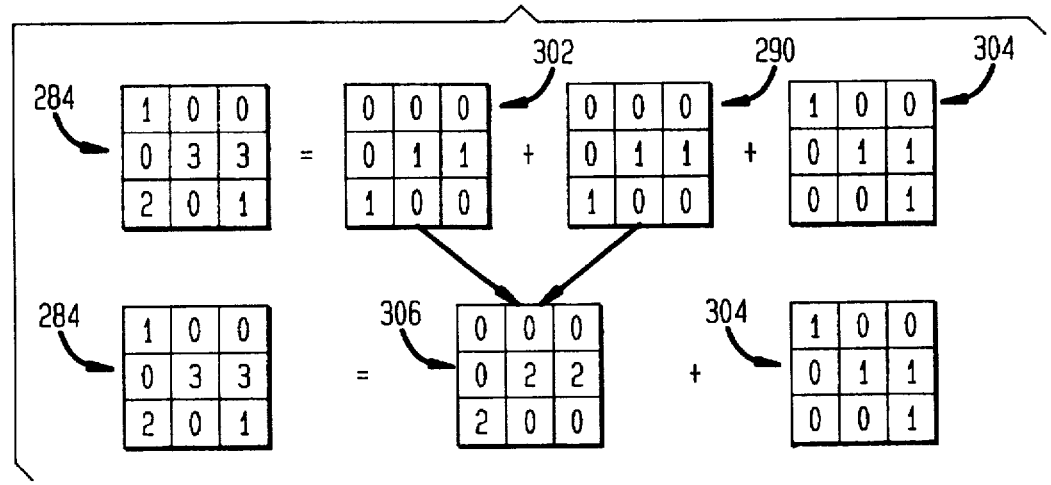

FIGS. 7A–C show matrices used for the section optimization process. Turning first to FIG. 7A, matrix 280 is a matrix which represents the field to be treated with radiation. In this example of the section optimization process, matrix 280 is initially broken up into two separate matrices 282 and 284. Minimum intensity matrix 282 is the largest possible cube-like matrix. Variation matrix 284 is the second matrix which includes the values left over after matrix 282 is removed from matrix 280. Matrix 284 is then broken down into three matrices 288, 290 and 292. These matrices 288, 290 and 292 contain only 1s and 0s. To begin the simplification process, matrix 288 is broken down into matrices 294 and 296.

In FIG. 7B, matrices 292 and 296 are combined to produce matrix 300, and matrix 288 is replaced by matrix 294. Matrix 284 now equals the sum of matrices 294, 290 and 300. In FIG. 7C, the upper left bit in matrix 294 (see FIG. 7B) is moved to the upper left position in matrix 300 (see FIG. 7B) to produce matrices 302 and 304. Now matrix 284 equals the sum of matrices 302, 290 and 304. Matrices 302 and 290 are then combined to produce matrix 306. Matrix 284 is now broken down into only two matrices 306 and 304. Overall, original matrix 280 can be broken down into three matrices 282, 306 and 304. Each of these three matrices 282, 306 and 304 represent a section of the field. Therefore, the field in this example is divided into three separate sections.

In the preferred embodiment, the plate position, radiation dose rate and time of radiation exposure are used to treat each of the sections with radiation. The plates are positioned over each section during the treatment of each section. A multi-leaf collimator can also be used instead of or in addition to the plates. If a multi-leaf collimator is used, strange shaped matrices can be easily covered by the radiation beam. Ten, 1 cm width leaves could be used in the multi-leaf collimator. Unfortunately, multi-leaf collimators usually have some radiation leakage which occurs between the leaves. If the plates are used, this radiation leakage is avoided. Therefore, it is advantageous to use the plates without the leaves a much as possible. Certain section arrangement allows for extensive use of the plates with a minimum use of the collimator leaves. This occurs when most of the sections are rectangular in shape. In addition, radiation leakage is greater when the leaves are moving during treatment. In the present invention, the leaves are not moving because they are treating small static sections of fields. Complete coverage of the field can also take place without changing the gantry position during treatment of a section. The stationary leaves and gantry (1) eliminate the need for dynamic control electronics because of the enhanced reliability of the treatment delivery and (2) allow non-coplanar intensity modulated fields to be delivered to the field to be treated. These non-coplanar intensity modulated fields do not have to lie in the same plane, and they are characterized by varying amounts of monitor units over the irradiation area. By allowing these fields to be non-coplanar and allowing intensities to vary across the field, healthy tissue will receive less radiation, and sensitive organs can be avoided.

The radiation delivered to an object may be analyzed into primary and scattered components. The primary radiation is made up of the initial or original photons emitted from the radiation source, and the scattered radiation is the result of the photons scattered by the plate arrangement itself. The beam's radiation output in free space increases because of the increased plate/collimator scatter, which is added to the primary beam. In other words, a point in the field is subjected not only to direct radiation (which is the primary component), but also to radiation that is scattered from the plate arrangement. Smaller fields have less radiation scatter. Therefore, when multiple sections are used to treat a field with radiation, the scatter is greatly reduced.

I claim:

1. A method for controlling radiation output delivered to an object from a radiation source, comprising the following steps:

defining a field on the object for irradiation;

dividing the field into multiple sections, each of the multiple sections having defined parameters; and treating each of the sections individually with radiation, the treating comprising the steps of:

defining an opening between the radiation source and the object, the opening being placed over one of the sections, the opening capable of delimiting the radiation beam to the defined parameters of the one of the sections; and generating a radiation beam having a substantially lossless beam path from a radiation source to the object, the radiation beam irradiating the one of the sections;

wherein the treating is repeated until each of the sections has been irradiated.

2. The method for controlling radiation output delivered to an object from a radiation source of claim 1, further comprising the step of varying the radiation output from the radiation beam.

3. The method for controlling radiation output delivered to an object from a radiation source of claim 1, wherein the opening is defined by at least one plate, the plate being capable of blocking radiation from the radiation source.

4. The method for controlling radiation output delivered to an object from a radiation source of claim 1, wherein the multiple sections are static sections.

5. The method for controlling radiation output delivered to an object from a radiation source of claim 1, further comprising the step of using matrices to divide the field into the multiple sections.

6. The method for controlling radiation output delivered to an object from a radiation source of claim 5, further comprising the step of organizing the matrices into a specific order.

7. The method for controlling radiation output delivered to an object from a radiation source of claim 1, wherein the opening is defined by a multi-leaf collimator, the multi-leaf collimator being capable of blocking radiation from the radiation source.

8. The method for controlling radiation output delivered to an object from a radiation source of claim 7, wherein an optimization routine is used for the dividing of the field.

9. The method for controlling radiation output delivered to an object from a radiation source of claim 1, wherein at least one of the sections is a rectangle.

10. A method for controlling radiation output delivered to an object from a radiation source, the radiation source being capable of generating a radiation beam, the method comprising the steps of:

inputting parameters of a field on the object for irradiation;

dividing the inputted field into multiple sections, the multiple sections having defined parameters;

positioning an opening over one of the sections, the opening being between the radiation source and the object, and the opening being capable of delimiting the radiation beam to the defined parameters of each of the sections;

treating each of the multiple sections individually with radiation.

11. The method for controlling radiation output delivered to an object from a radiation source of claim 10, further comprising the step of defining radiation dose at the isocenter of each of the sections.

12. The method for controlling radiation output delivered to an object from a radiation source of claim 10, wherein an optimization routine is used for the dividing of the inputted field.

13. The method for controlling radiation output delivered to an object from a radiation source of claim 10, wherein the opening is defined by at least one plate, the plate being capable of blocking radiation from the radiation source.

14. A system for controlling radiation output delivered to a field to be irradiated on an object, comprising:

a radiation source for generating a radiation beam;

beam-shielding means for delimiting the output radiation beam to predetermined parameters;

a dose controller for varying an amount of the radiation output from the radiation source; and processing means for dividing the field to be irradiated into multiple sections, each of the sections having defined parameters;

wherein each of the multiple sections are treated individually with radiation.

15. The system for controlling radiation output delivered to a field to be irradiated on an object of claim 14, wherein the processing means uses matrices to divide the field into the multiple sections.

16. The system for controlling radiation output delivered to a field to be irradiated on an object of claim 15, wherein the matrices are organized into a specific order, the order being dependent on the movement of the beam-shielding means.

17. The system for controlling radiation output delivered to a field to be irradiated on an object of claim 14, wherein the beam-shielding means are at least one of plates and a collimator.

18. The system for controlling radiation output delivered to a field to be irradiated on an object of claim 14, wherein at least one of the sections is a rectangle.

19. The system for controlling radiation output delivered to a field to be irradiated on an object of claim 14, wherein an optimization routine is used by the processing means.

* * * * *